United States Patent [19]
Calabrese

[11] 3,957,040
[45] May 18, 1976

[54] CERVICAL BRACE

[75] Inventor: Anthony Calabrese, Philadelphia, Pa.

[73] Assignee: Charles Greiner & Company, Philadelphia, Pa.

[22] Filed: Dec. 16, 1974

[21] Appl. No.: 533,059

[52] U.S. Cl. .............................. 128/75; 128/87 B
[51] Int. Cl.² .......................................... A61H 1/02
[58] Field of Search ............... 128/75, 78, 84, 87 R, 128/87 B, 89 R, 89 A, DIG. 23

[56] References Cited
UNITED STATES PATENTS

| | | | |
|---|---|---|---|
| 443,764 | 12/1890 | Hilliard | 128/78 |
| 678,417 | 7/1901 | Muller | 128/89 A |
| 2,474,200 | 6/1949 | McBee | 128/DIG. 23 |
| 2,672,146 | 3/1954 | Touson | 128/89 A |
| 2,796,866 | 6/1957 | Cohen | 128/DIG. 23 |
| 2,820,455 | 1/1958 | Hall | 128/87 A |
| 3,336,922 | 8/1967 | Taylor | 128/75 |
| 3,669,102 | 6/1972 | Harris | 128/84 R |

*Primary Examiner*—John D. Yasko
*Attorney, Agent, or Firm*—Seidel, Gonda & Goldhammer

[57] ABSTRACT

A cervical brace is disclosed for applying traction to a person's head without contacting the skin by pins and without contacting the jaw whereby the ability of the patient to talk or eat is not impaired. The person's head may be maintained in a predetermined angular position by three longitudinally adjustable rigid members each having their ends pivotably supported by discrete portions of the brace.

12 Claims, 7 Drawing Figures

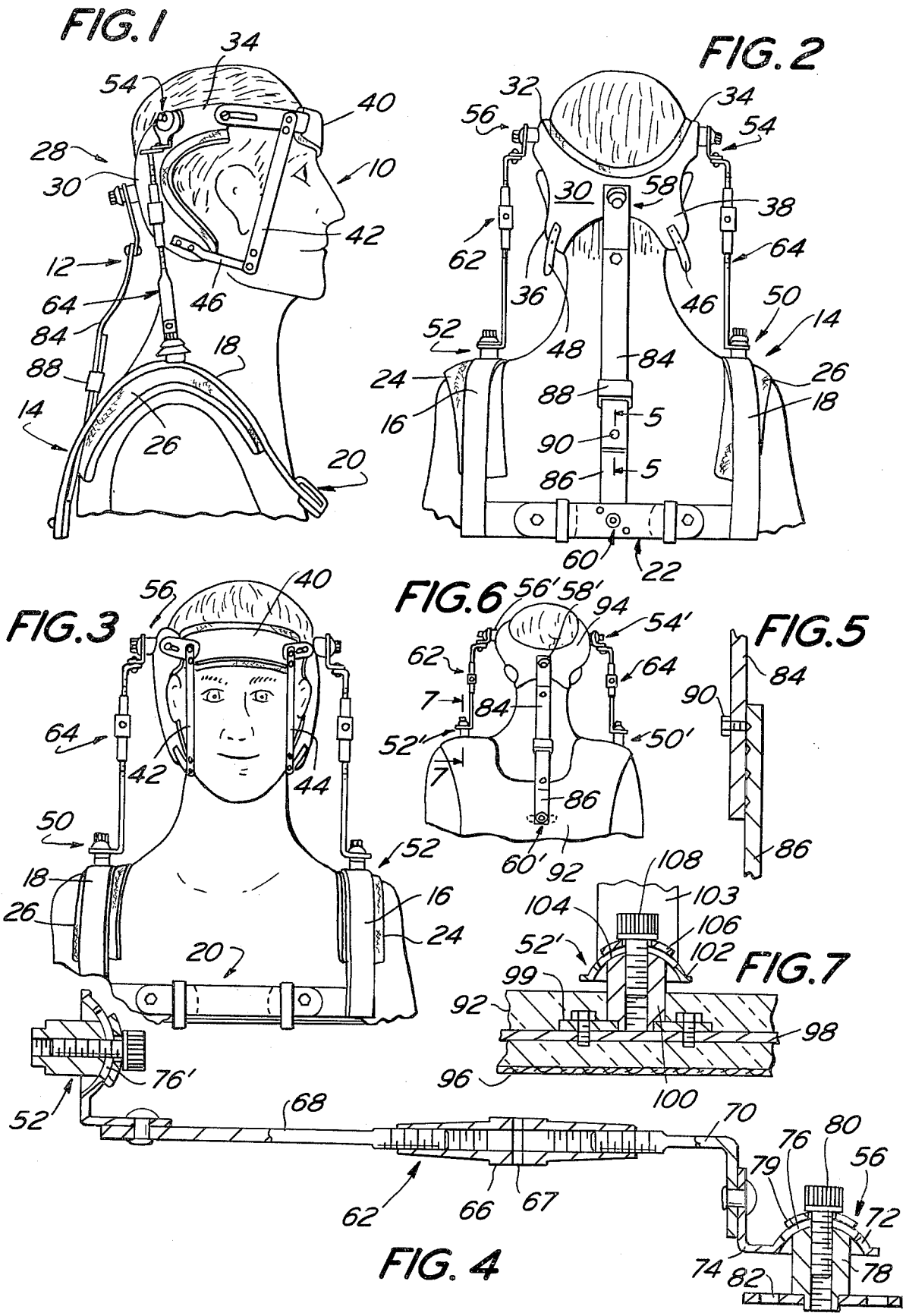

CERVICAL BRACE

BACKGROUND

The invention is directed to a cervical brace of the type which applies traction to a person's head for a purpose such as relieving pressure at a pinched nerve. Heretofore, a large number of cervical braces have been suggested and they fall generally into two categories.

U.S. Pat. Nos. 1,301,276 and 3,548,817 are typical of a first category of prior art cervical braces wherein a portion of the brace engages the jaw of the person so that traction may be applied to the person's head. A cervical brace of that type which engages the person's jaw has undesirable attributes in that the ability of the person to eat and/or talk in a normal manner is substantially impaired.

U.S. Pat. Nos. 3,336,922 and 3,669,102 are typical of a second category of prior art cervical braces and referred to in the trade as being of the halo type. As disclosed in said patents, a portion surrounds the person's head and is spaced therefrom. Contact with the person's head is made by pointed screws adjustably supported by the halo. Adjustment of the screws determines the predetermined position of the person's head. If the person attempts to move from the predetermined position, his skin is pierced by the pointed screws. Aside from the pain which must be endured by the patient, a further disadvantage of such halo prior art cervical braces is the necessity to be constantly cognizant of potential infection to the person's head at the points where the skin is broken by the pointed screws.

The present invention is directed to a cervical brace having two body contacting portions, namely a shoulder embracing portion and a head embracing portion. The head embracing portion is curved at one location for engaging the lower rear of a person's head in the area of the occipital bone and has a forehead engaging portion.

The cervical brace of the present invention includes a means for pivotably connecting three spaced locations on the shoulder embracing portion to three spaced mating locations on the head embracing portion. Said means includes three longitudinally adjustable rigid members. Each end of each rigid member is pivotably connected to one of said shoulder and head embracing portions.

A more specific description of the cervical brace of the present invention is as follows. The brace comprises a shoulder embracing portion adapted to overlie each shoulder of a person. First and second pivot mounts are provided on said shoulder bracing portion in a manner so that each mount will be supported in a location so as to be over a discrete shoulder of a person. The brace also includes a curved head engaging portion for engaging the lower rear of a person's head adjacent the occipital bone with a forehead engaging portion extending therefrom. Each of the shoulder and head engaging portions may be preassembled and manufactured components or may be a cast worn by the person.

Third and fourth pivot mounts are supported by the head engaging portion and extend outwardly from opposite sides of the outer periphery thereof. A fifth pivot mount is provided on the head engaging portion substantially equidistant from the third and fourth pivot mounts and at an elevation below the elevation of the third and fourth pivot mounts. A sixth pivot mount is provided on the shoulder embracing portion between and at an elevation below the elevation of the first and second mounts.

Three longitudinally adjustable rigid members are provided for interconnecting the shoulder and head engaging portions of the brace. One of said rigid members is pivotably connected at its ends to said first and third mounts. A second of said rigid members is pivotably connected at its ends to said second and fourth mounts. A third of said rigid members is pivotably connected at its ends to said fifth and sixth mounts.

It is an object of the present invention to provide a cervical brace which is versatile, easily adjusted, and more comfortable for the person wearing the same.

It is another object of the present invention to provide a cervical brace which permits application of traction to a person's head without piercing the skin or contacting the jaw whereby the ability of the person to talk and/or eat is not impaired.

Other objects will appear hereinafter.

For the purpose of illustrating the invention, there is shown in the drawings a form which is presently preferred; it being understood, however, that this invention is not limited to the precise arrangements and instrumentalities shown.

FIG. 1 is a side elevation view of a person wearing a cervical brace in accordance with the first embodiment of the present invention.

FIG. 2 is a rear elevation view of the brace shown in FIG. 1.

FIG. 3 is a front elevation view of the brace shown in FIG. 1.

FIG. 4 is a longitudinal sectional view of a rigid adjustable member extending between the shoulder and head engaging portions of the brace.

FIG. 5 is a sectional view taken along the line 5-5 in FIG. 2.

FIG. 6 is a rear elevation view of a cervical brace in accordance with another embodiment of the present invention.

FIG. 7 is a sectional view taken along the line 7-7 in FIG. 6 but on an enlarged scale.

Referring to the drawing in detail, wherein like numerals indicate like elements, there is shown in FIG. 1 a person 10 wearing a cervical brace 12 in accordance with the present invention. As will be apparent from FIGS. 1 and 3, the cervical brace 12 does not engage the jaw of the person 10 and therefore does not impair the ability of the person to consume food and/or engage in conversation. These advantages will be immediately perceived by those who have worn prior art cervical braces.

The cervical brace 12 of the present invention includes discrete body engaging portions interconnected at a plurality of locations by longitudinally adjustable rigid members as will be described in greater detail hereinafter. The first of the body engaging portions is the shoulder engaging portion 14.

The shoulder engaging portion 14 shown in FIGS. 1-3 is a prefabricated structure having shoulder straps 16 and 18 adapted to overlie the shoulder of the person 10. The free ends of the straps 16 and 18 are interconnected at the front by an adjustable front strap 20 and at the rear by an adjustable rear strap 22. If desired, the front and rear straps 20 and 22 may be interconnected by a member which extends below the armpit of the person 10 on opposite sides thereof. Such interconnection below the armpits of the person 10 is optional. The front and rear straps 20 and 22 are adjustable so that they may accomodate to persons of different sizes. A cushion pad 24 is preferably provided beneath the shoulder strap 16 and a similar pad 26 may be provided beneath the strap 18.

The second body engaging portion of the brace 10 is the head engaging portion designated generally as 28. The head engaging portion 28 includes a rigid body 30 provided with a padded cushion on its inner periphery. The body 30 is provided with a concave recess on its lower surface with a larger concave recess on its upper surface as shown more clearly in FIG. 2 thereby defining temple projections 32, 34 and neck projections 36 and 38. The body 30 and its integral projections are curved so as to engage the head of the person 10 adjacent the occipital bone. It will be noted that the body 10 does not overlie the ears of the person 10 and therefore does not interfere with his hearing.

A padded member 40 extends across the forehead of the person 10 and is adjustably connected at its ends to the temple projections 32, 34 in any conventional manner. An extension 46 on the neck projection 38 is adjustably and releasably connected to the forehead member 40 by way of a flexible strap 42. A similar strap 44 interconnects the extension 48 on the neck projection 36 with the forehead member 40. Depending upon the shape and size of a person's head, straps 42 and 44 may be omitted. The straps 42 and 44 apply an inward force on the temple projections 36 and 38 so as to prevent the body 30 from moving upwardly along the back of the head of the person 10.

The brace 12 includes a plurality of spaced pivot mounts including a first pivot mount 50 and a second pivot mount 52 on the shoulder straps 18 and 16 respectively; third and fourth pivot mounts 54 and 56 on opposite sides of the outer periphery of the body 30; a fifth pivot mount 58 on the body 30 between and at an elevation below the elevation of mounts 54, 56; and a sixth pivot mount 60 on the rear strap 22 of the shoulder engaging portion 14 so as to be between and below the elevation of the first and second mounts 50, 52.

Each of the pivot mounts 50–60 are identical. Hence, only pivot mount 56 will be described in detail. Sets of said pivot mounts are interconnected by longitudinally adjustable rigid members. The first and third pivot mounts 50, 54 are interconnected by member 64. The second and fourth mounts, 52, 56 are interconnected by member 62. The member 62 and 64 are identical. Accordingly, only member 62 will be described in detail in conjunction with the pivot mount 56.

As shown more clearly in FIG. 4, the longitudinally adjustable rigid member 62 includes a turnbuckle 66 threadedly coupled to the ends of members 68 and 70. One of the sets of mating threads are right hand threads while the other is left hand threads. The turnbuckle 66 has a hole 67 therethrough to facilitate receipt of a tool to rotate the turnbuckle and thereby increase or decrease the effective length of the member 62.

The unthreaded end of member 70 is rigidly secured to a projection 74 on a concave semi-spherical plate 72. In the center of the plate 72, there is provided an elongated slot 76. The semi-spherical surface on plate 72 cooperates with a mating surface on one end of a saddle 78. A bolt 80 extends through a semi-spherical washer 79, through the slot 76, and is threaded to the saddle 78. As a result of the semi-spherical mating surfaces of plate 72 and saddle 78, these two parts can be pivoted relative to each other in a first plane which is perpendicular to the axis of the bolt 80. In addition, the slot 76 allows plate 72 and saddle 78 to be pivoted with respect to each other in a second plane which extends in the direction of slot 76 and parallel with the axis of bolt 80. Thus, it can be seen that plate 72 and saddle 78 can be pivoted in two mutually perpendicular planes. One end of the saddle 78 is fixedly secured to a support plate 82 which is embedded in the temple projection 32 of the body 30.

The slot 76 is elongated in a direction corresponding to the longitudinal axis of the turnbuckle 66. The pivot mount 52 is identical with the pivot mount 56 with the exception that the elongated slot 76' is elongated in a direction which is perpendicular to the longitudinal axis of turnbuckle 66.

The longitudinally adjustable rigid member for interconnecting the pivot mounts 58 and 60 includes a pair of overlapping bar members 84 and 86. Member 84 extends through a loop 88 on the bar member 86. Member 84 is connected to the pivot mount 58 in the same manner that member 70 is connected to pivot mount 56. The bar member 86 is connected to the pivot mount 60 in the same manner that member 68 is connected to the pivot mount 52. A set screw 90 cooperates with the row of indentations on member 86 to retain the members 84 and 86 in any predetermined position. See FIG. 5.

The pivot mounts and the longitudinal adjustability of the members 62, 64, 84 and 86 enable the brace 10 to be applied for maintaining the head of the person 10 in various selected positions while applying traction between the head and shoulders. Thus, the head of the person 10 may be tilted to the right or left in FIG. 2, or tilted forwardly or rearwardly in FIG. 1.

The body engaging portions of the brace need not be prefabricated as described above. Thus, the shoulder engaging portion may be a cast 92 applied in situ to the body of the person 10. Likewise, a head engaging cast 94 may be applied to the person 10 in situ. The cast 92 and 94 are applied in a conventional manner except that six pivot mounts 50', 52', 54', 56', 58' and 60' are applied to the casts in the same general location as described above. Each of the last mentioned pivot mounts is identical with those described above and exemplified by pivot mount 52' shown in FIG. 7.

Referring to FIG. 7, the cast 92 is applied to the body over a layer of fabric 96 with a metal reinforcement layer 98 therewithin. A support member 99 for the saddle 100 is fixedly secured to the reinforcing layer 98 disposed within the cast 92. The saddle 100 is of sufficient axial length so as to be projecting from the cast 92 directly over the shoulder of the person. Casts 92, 94 are of plaster or other suitable material.

A concave semi-spherical plate 102 is connected to a rod member, comparable to member 68, by way of a projection 103. Slot 104 in member 102 is elongated in a direction from front to back with respect to the person. A bolt 108 extends through a semi-spherical washer 106, through the slot 104, and is threadedly connected to the saddle 100.

Thus, the embodiment shown in FIGS. 6 and 7 enables a person to have two body engaging casts applied in situ with each having three pivot mounts projecting therefrom. Thereafter, the longitudinally adjustable rigid members 62, 64, 84 and 86 are attached to the three mating sets of pivot mounts to complete the brace.

The longitudinally adjustable rigid members, and the reinforcing layers or supports for insertion into the castings are preferably made from a lightweight rigid noncorrosive material such as aluminum. The cost of a cervical brace may be substantially reduced as per FIGS. 6 and 7 since only the above described three sets of pivot mounts, the reinforcements for the pivot mounts, and the longitudinally extending rigid members are needed to complete a cervical brace with the casts 92 and 94. In each of the embodiments set forth above, there are no pointed screws for contact with the skin and the jaw of the patient is free at all times to permit the patient to consume food or talk. Further, the ability of the patient to utilize his jaw in a normal manner facilitates consumption of medicine orally which otherwise may have to be applied intravenously.

The bolts 80 and 108 are preferably provided with circular heads contaning on their end faces a noncircular recess for adjustment by a mating allen head wrench. In this manner, the patient will have great difficulty in making any adjustments in the settings whereas the doctor will be able to make any such adjustments with ease.

In order to accomodate the various angular positions in which the head may be fixedly held while in traction, it is preferred to have the slots of the pivot mounts 50 and 52 elongated in a direction from front to back while the slots in the pivot mounts 54, 56 are elongated in a vertical direction. The mating spherical surfaces on each of the pivot mounts readily accomodates to the proper and desired positioning of the patient's head. It will be obvious that the bolt associated with each pivot mount is loosened to facilitate adjustment and then retightened.

The present invention may be embodied in other specific forms without departing from the spirit or essential attributes thereof and, accordingly, reference should be made to the appended claims, rather than to the foregoing specification as indicating the scope of the invention.

I claim:

1. A cervical brace including a shoulder embracing portion and a head embracing portion, a part of said head embracing portion extending in the form of a loop so that it may overlie the forehead of a person, said head embracing portion being free from any component for engaging a jaw of a person, and means for pivotably connecting said shoulder and head embracing portions together at three spaced locations, said means including three longitudinally adjustable rigid members each of which having its ends pivotably supported by a discrete portion of said shoulder and head embracing portions.

2. A cervical brace in accordance with claim 1 wherein each end of each of said rigid members is pivotably connected to one of said shoulder and head embracing portions by a pivot mount.

3. A cervical brace in accordance with claim 2 wherein each pivot mount includes mating semi-spherical surfaces.

4. A cervical brace in accordance with claim 3 wherein two of said pivot mounts which are adapted to overlie the shoulder of a person include an elongated slot in one of said semi-spherical surfaces, said slots being elongated in a direction from front to rear, and two of said pivot mounts on said head embracing portion having slots in one of said semi-spherical surfaces and which are elongated in a vertical direction, said two pivot mounts on said head embracing portion extending outwardly in a horizontal direction from opposite sides of the periphery of said head embracing portion, said two pivot mounts on said shoulder embracing portion extending upwardly therefrom.

5. A cervical brace in accordance with claim 1 wherein each end of each of said rigid members is pivotably connected to one of said shoulder and head embracing portions by a means which allows said end and said one of said shoulder and head embracing portions to be pivoted with respect to each other in two mutually perpendicular planes.

6. A cervical brace in accordance with claim 5 wherein each end of each of said rigid members is pivotably connected to one of said shoulder and head embracing portions by a pivot mount having mating semi-spherical surfaces.

7. A cervical brace for applying traction to a person's head comprising
   a. A shoulder embracing portion adapted to overlie each shoulder of a person, said portion having first and second pivot mounts, each pivot mount being supported by said shoulder embracing portion in a location thereon so as to be over a shoulder of a person,
   b. A curved head engaging portion for engaging a person's head adjacent the occipital bone and for engaging a person's forehead,
   c. Third and fourth pivot mounts, said third and fourth pivot mounts being supported by said head engaging portion and extending outwardly in a generally horizontal direction from opposite sides of the outer periphery thereof, a fifth pivot mount on said head engaging portion, said fifth pivot mount being located approximately equidistant from and below the elevation of said third and fourth pivot mounts,
   d. A sixth pivot mount on said shoulder embracing portion between and at an elevation below the elevation of said first and second pivot mounts,
   e. Three longitudinally adjustable rigid members, the first of said rigid members being pivotably connected at its ends to said first and third pivot mounts, a second of said rigid members being pivotably connected at its ends to said second and fourth pivot mounts, and a third of said rigid members being pivotably connected at its ends to said fifth and sixth pivot mounts.

8. A cervical brace in accordance with claim 7 wherein each of said pivot mounts includes mating semi-spherical surfaces adjustably positionable with respect to each other.

9. A cervical brace in accordance with claim 8 wherein one of the semi-spherical surfaces on said first and second pivot mounts includes a slot elongated in a direction from front to rear, and one of the spherical surfaces associated with said third and fourth pivot mounts having a slot elongated in a vertical direction.

10. A cervical brace in accordance with claim 7 wherein said shoulder engaging portions includes prefabricated metal members adapted to extend over the shoulders of a person and interconnected at their ends by front and rear adjustable members.

11. A cervical brace in accordance with claim 7 wherein said first and second pivot mounts are connected to a metal reinforcing layer forming a part of the shoulder embracing portion.

12. A method of applying a cervical brace comprising the steps of applying a shoulder cast to a person with three pivot mounts embedded in the cast in a manner so that a pivot mount extends upwardly from each shoulder with the remaining pivot mount extending generally horizontally from the back of the cast at an elevation below the shoulder, applying a head engaging cast extending from the forehead to a region opposite the occipital bone in a manner so as to have three pivot mounts projecting therefrom with two pivot mounts extending generally horizontally outwardly from opposite sides of the outer periphery of the head cast and the remaining pivot mount extending rearwardly from the head cast generally in line with the pivot mount on the back of the shoulder cast, and then joining each shoulder located pivot mount with a mating pivot mount on the head cast by a longitudinally adjustable rigid member pivotably connected at its ends to the associated pivot mounts, and interconnecting the pivot mounts extending from the rear of the head and shoulder casts by a longitudinally adjustable rigid member pivotably connected thereto at its ends.

* * * * *